(12) United States Patent
Van Den Hoogenhof et al.

(10) Patent No.: US 9,851,313 B2
(45) Date of Patent: Dec. 26, 2017

(54) QUANTITATIVE X-RAY ANALYSIS—RATIO CORRECTION

(71) Applicant: PANalytical B.V., Almelo (NL)

(72) Inventors: Waltherus Van Den Hoogenhof, Almelo (NL); Charalampos Zarkadas, Almelo (NL)

(73) Assignee: PANALYTICAL B.V., Almelo (NL)

(*) Notice: Subject to any disclaimer, the term of this patent is extended or adjusted under 35 U.S.C. 154(b) by 204 days.

(21) Appl. No.: 14/636,938

(22) Filed: Mar. 3, 2015

(65) Prior Publication Data

US 2016/0258889 A1 Sep. 8, 2016

(51) Int. Cl.
*G01N 23/20* (2006.01)
*G01N 23/22* (2006.01)
*G01N 23/223* (2006.01)
*G01N 23/207* (2006.01)

(52) U.S. Cl.
CPC ......... *G01N 23/2206* (2013.01); *G01N 23/20* (2013.01); *G01N 23/207* (2013.01); *G01N 23/223* (2013.01); *G01N 2223/071* (2013.01)

(58) Field of Classification Search
CPC ....... G01N 2223/076; G01N 23/20066; G01N 23/223
See application file for complete search history.

(56) References Cited

U.S. PATENT DOCUMENTS

| | | | | | |
|---|---|---|---|---|---|
| 3,855,470 A | * | 12/1974 | Sahores | .................. | G01N 23/20 378/73 |
| 5,132,997 A | * | 7/1992 | Kojima | ................ | G01N 23/223 378/49 |
| 5,155,751 A | * | 10/1992 | Chohata | .................... | C23C 2/28 378/70 |
| 5,579,362 A | * | 11/1996 | Matsuura | ............... | G01B 15/02 378/59 |
| 6,512,810 B1 | * | 1/2003 | Haszler | .................. | G01B 15/02 378/45 |
| 6,821,361 B2 | * | 11/2004 | Fujimura | ............. | G01N 23/207 148/508 |
| 7,120,226 B2 | * | 10/2006 | Ledoux | ................ | G01N 23/223 250/307 |
| 7,247,627 B2 | * | 7/2007 | Blasko | ................. | C07D 403/06 514/231.2 |
| 7,300,900 B2 | * | 11/2007 | Benazzi | ................... | B01J 29/80 502/66 |

(Continued)

FOREIGN PATENT DOCUMENTS

EP 2 315 009 4/2011

OTHER PUBLICATIONS

H Gupla et al., "Quantitative Analysis: An Empirical Approach", 1995, Received Apr. 5, 1994, pp. 755-760, XP055285974, Retrieved from the Internet: URL:http://ac.els-cdn.com/0956716X9591598J/1-s2.0-0956716X9591598J-main.pdf?_tid=65fa10ca-42a9-11e6-9af6-00000aacb35d&acdnat=1467720781_821c58516f18dd5le5714aa78d664313 [retrieved on Jun. 5, 2016].

*Primary Examiner* — David J Makiya
*Assistant Examiner* — Soorena Kefayati
(74) *Attorney, Agent, or Firm* — Leason Ellis LLP (57) ABSTRACT

A method of X-ray analysis measures X-ray diffraction in transmission. In order to carry out quantitative measurements, a background measurement is taken slightly away from the diffraction peak and the ratio of measured intensities used to correct for variations in sample composition.

9 Claims, 5 Drawing Sheets

(56) References Cited

U.S. PATENT DOCUMENTS

| | | | | |
|---|---|---|---|---|
| 7,471,766 B2* | 12/2008 | Dosho | ............... | G01N 23/20 |
| | | | | 378/71 |
| 7,720,192 B2* | 5/2010 | Hegeman | ............ | G01N 23/223 |
| | | | | 378/44 |
| 7,978,820 B2* | 7/2011 | Kharchenko | .... | G01N 23/20091 |
| | | | | 378/44 |
| 8,703,335 B2* | 4/2014 | Pitteloud | ............ | C01G 45/1228 |
| | | | | 429/221 |
| 9,086,367 B2* | 7/2015 | Mitsunaga | ........... | G01N 23/207 |
| 9,146,204 B2* | 9/2015 | Fukuda | ............... | G01N 23/223 |
| 9,187,814 B2* | 11/2015 | Nose | .................... | B32B 15/012 |
| 9,448,191 B2* | 9/2016 | Utaka | ................ | G01N 23/2206 |
| 2003/0085350 A1* | 5/2003 | Kaji | ...................... | G01N 23/04 |
| | | | | 250/305 |
| 2009/0210366 A1* | 8/2009 | Sakata | ................... | G01N 23/20 |
| | | | | 706/13 |
| 2015/0055756 A1* | 2/2015 | Nakazawa | ............... | C23C 2/06 |
| | | | | 378/71 |
| 2015/0298981 A1* | 10/2015 | Burton | ................... | C01B 37/02 |
| | | | | 585/250 |
| 2015/0338534 A1* | 11/2015 | Mizuno | ............... | G01N 23/223 |
| | | | | 378/45 |

\* cited by examiner

QUANTITATIVE X-RAY ANALYSIS—RATIO CORRECTION

FIELD OF INVENTION

The invention relates to a method of quantitative X-ray analysis and apparatus for carrying out the method.

BACKGROUND TO THE INVENTION

Materials analysis using X-rays provides accurate data in a number of applications and industries. X-ray fluorescence measurements allow the determination of the elemental composition of a sample. In some applications however this is not enough and there is a need not merely to determine the elemental composition but also to determine structure parameters such as the crystalline phases of a sample and X-ray diffraction is used in these cases.

Typically, high resolution X-ray diffraction measurements are carried out in reflection mode, where an incoming beam of X-rays is incident on a first surface of a sample and the X-rays diffracted by a diffraction angle $2\theta$ from the same surface of the sample are detected by a detector.

In some applications it is useful to be able to take X-ray diffraction measurements in a transmission mode, where the X-rays are incident on a first surface of a sample and diffracted by a diffraction angle $2\theta$ are measured after passing through the sample from the first surface to the opposite second surface.

A problem with making measurements in this transmission geometry is that the sample itself may be absorbing for X-rays. Therefore, it is difficult to carry out accurate quantitative analysis of the diffracted X-rays to determine the amount of any given phase of the sample, since the absorption of X-rays in the sample is not in general known.

There is therefore a need for a method that quantitatively carries out a matrix and thickness correction for X-ray diffraction.

Absorption of electromagnetic waves that pass directly through a medium is characterised by the Beer-Lambert law $$I = I_0 e^{-\mu\rho d}$$

where $I_0$ is the original intensity, I the intensity after passing through the material, $\mu$ the mass attenuation coefficient of the material, $\rho$ the material density and d the material thickness (i.e. the ray path length in the material).

The calculation of the effects of absorption in quantitative X-ray measurements is made more difficult than this simple formula would suggest for a number of reasons.

In the simple Beer-Lambert case where X-rays pass directly through a sample without deviation it is possible to characterise the effect of the absorption on the measured X-ray intensity simply by a single value, the value of the product $\mu\rho d$. This is not possible where the X-rays of interest are diffracting X-rays or otherwise redirected and to accurately characterise the absorption requires two parameters, the product $\mu\rho d$ as well as the mass absorption coefficient $\mu$.

In this regard, some samples have constraints on thickness. For a pressed powder sample, a suitable thickness of the sample that will result in a sample that is sufficiently strong to be handled and measured will be at least 2 mm, preferably 3 mm. However, at these thicknesses, for typical X-ray energies required for many applications, the absorption of X-rays in the thickness of a sample is higher than 50%. This means that the effects of absorption are large and any deviances from the simple Beer-Lambert law significant. A large absorption means that the relationship between measured intensity and concentration of a particular component of a sample is not straightforward.

A further problem is that the absorption is a function of the composition of the sample. Small changes in the concentration of various components in the sample can cause significant changes in absorption. This is a problem for quantitative X-ray analysis designed to measure the quantity of a given component in the sample, since the amount of that component is unknown but will affect the absorption.

A yet further problem when measuring pressed powder samples is that the thickness d is not generally exactly known. In general, in an industrial environment, it will be desired to make a pressed powder sample and then measure it as soon as possible. It is generally undesirable to have to make accurate measurements of thickness d before carrying out X-ray measurement.

Figure 1:
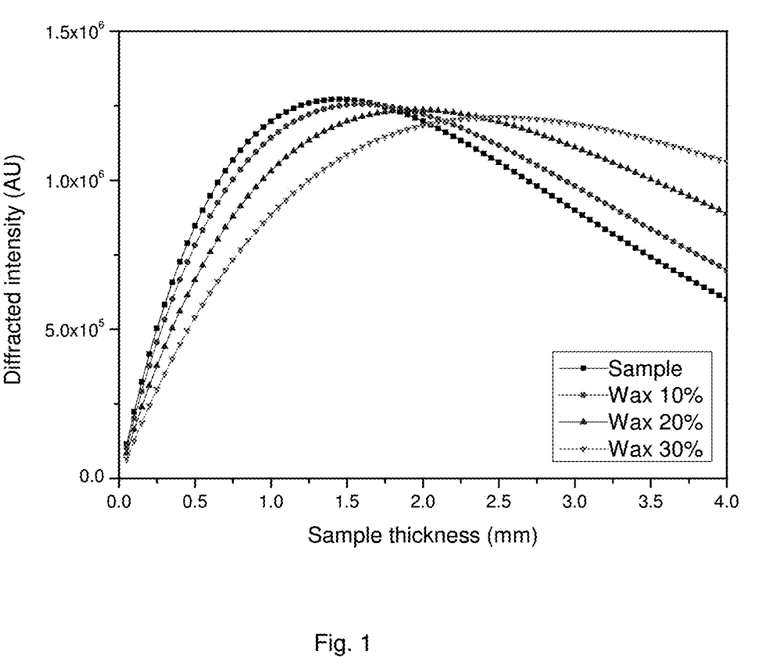
FIG. 1 is a graph of measurement intensity against thickness for samples of different concentrations of powder in wax.

These difficulties may be seen with reference to FIG. 1 which illustrates the theoretically calculated diffraction intensity for free lime as a function of sample thickness for three samples of standard cement clinker materials (Portland cement clinker) mixed with a wax binder for various binder percentages of 0%, 10%, 20% and 30%. Note that in spite of the fact that the samples of higher thickness contain more diffracting material—a sample of twice the thickness has twice the amount of free lime—the diffracted intensity is in fact less. Realistic sample thicknesses around 3 mm are in the highly non-linear regime in which there is no simple relationship between measured intensity and amount of free lime in the sample.

Figure 2:
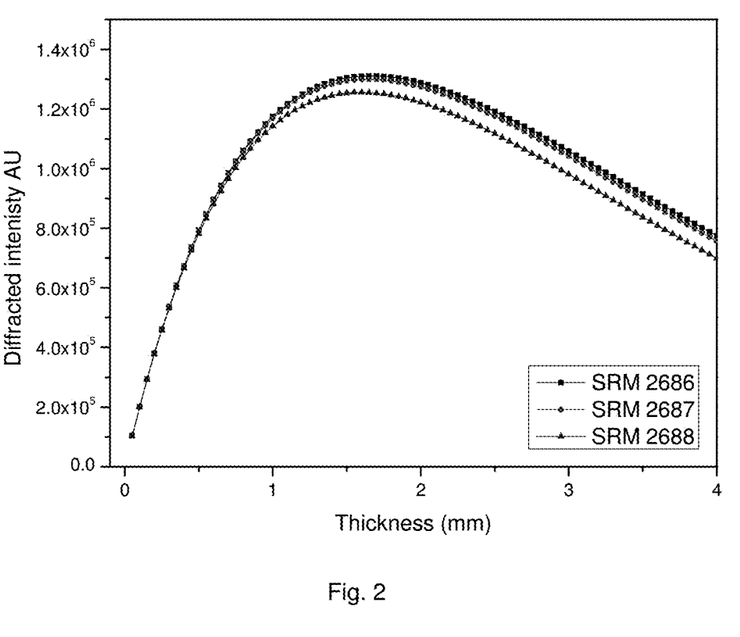
FIG. 2 is likewise a graph of measurement intensity against thickness for samples of different composition.
Figure 3:
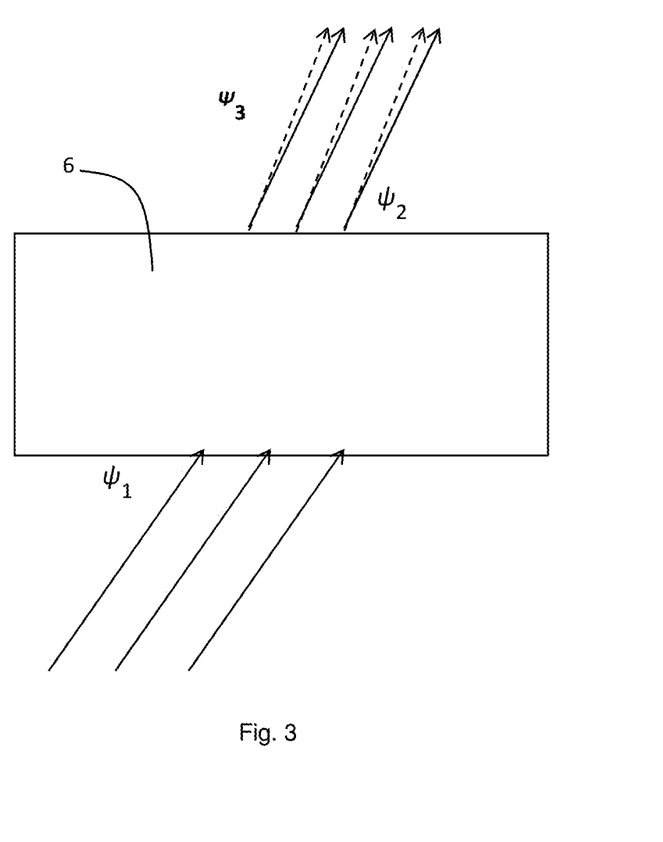
FIG. 3 is a schematic indicating incident and exit X-rays in a configuration considered below in the "theory" section.

Further, as illustrated in FIG. 2, the diffraction intensity is also dependent on the exact composition. FIG. 2 shows three graphs for three different samples each of Portland cement clinker. In spite of the general similarity between the samples, the diffraction intensity still varies from sample to sample illustrating that the effect of absorption is a function of the exact composition which varies from sample to sample. At a thickness of 3 mm a difference of about 8% in diffraction intensity is seen. This too makes calculating a quantitative measure of free lime concentration from diffraction measurements difficult.

The effects of a variable composition on quantitative measurement is known as a matrix correction since it depends on the composition of the measured sample, i.e. the matrix. It is in general difficult to calculate the matrix correction. There is therefore a need for a measurement method which avoids this difficulty.

SUMMARY OF THE INVENTION

According to the invention, there is provided a method of X-ray analysis comprising: making an X-ray diffraction measurement in transmission by directing X-rays from an X-ray source at an energy E onto a sample at an incident angle $\psi_1$ to the surface of the sample and measuring a diffraction intensity $I_d(\theta_d)$ of the diffracted X-rays at the energy E with a X-ray detector at an exit angle $\psi_2$ to the surface of the sample, the difference $2\theta_d$ between the incident angle and the exit angle corresponding to an X-ray diffraction peak of a predetermined component; and making a correction measurement of X-rays by measuring the background intensity of X-rays $I_d(\theta_{bg})$ at the energy E, with the difference $2\theta_{bg}$ between the incident angle and the exit angle deviating by 0.2 to 5° from the difference $2\theta_d$ corresponding to an X-ray diffraction peak; and calculating the quantity of the predetermined component from the intensity ratio of the diffraction intensity and the background intensity.

By carrying out measurements in this way, it is possible to cancel out the effects of the transmission through the sample and hence obtain quantitative measurements even in a transmission geometry. The theory of why the effects cancel out is presented below.

The step of making a correction measurement of X-rays may use incident X-rays directed onto the sample at the same incident angle $\psi_1$ to the angle used in the step of making an X-ray diffraction measurement and measures the background intensity of X-rays at an exit angle $\psi_3$ to the surface of the sample, where $\psi_3=\psi_2\pm\Delta\psi$ and $\Delta\psi$ is in the range 0.2 to 5°. By using a small deviation in the position of the collimator and detector it is possible to ensure that the same sample volume is seen for both measurements reducing any inaccuracy caused by inhomogeneity in this sample.

Calculating the quantity of the predetermined component may use a linear relation between the intensity ratio and a calculated $$W = \frac{w_{fl}}{1 - w_{fl}}$$

where $w_{fl}$ is the weight fraction of the component of interest. This substitution ends up with a linear calibration curve making it easier to carry out a fit.

Calculating the quantity of the predetermined component may obtain the quantity of the predetermined component from a calibration curve linking the intensity ratio to the quantity of the predetermined component The predetermined component may be free lime.

A calibration curve may be obtained by relating the intensity ratio to concentration of the predetermined component by carrying out a method as set out above for a plurality of samples each having a known concentration of the predetermined component.

The method may include fitting a straight line to the intensity ratio as a function of the concentration of the plurality of samples having a known concentration of the predetermined component.

In another aspect, the invention relates to an X-ray apparatus, comprising:

a sample stage for supporting a sample extending substantially horizontally;

an X-ray source located to direct X-rays to the sample stage;

an X-ray detector located on the other side of the sample stage for measuring X-ray intensity of diffracted X-rays in a transmission geometry; and a controller;

wherein the controller is arranged to cause the X-ray apparatus to carry out a method as set out above on a sample mounted on the sample stage.

The apparatus may further include a further X-ray system located on the same side of the sample stage as the X-ray source for making X-ray fluorescence measurements of the sample. This additional system can enable further measurements to be made without removing the sample from the apparatus allowing fuller characterisation of the sample.

BRIEF DESCRIPTION OF THE DRAWINGS

An example of the invention will now be described with reference to the accompanying diagrams, in which.

DETAILED DESCRIPTION

The invention relates to a method which can be applied for the correction of measured photon intensities in X-ray diffraction in transmission geometry without explicit knowledge of the sample's thickness.

Theory

XRD measurements performed in transmission geometry require that the measured specimens have finite thickness in order to allow the generated photons to escape the specimen from the back side and at a certain exit angle. Theoretical calculations predict that the measured photon intensity will depend both on sample thickness as well as on composition. In that sense the repeatability of the measurements with respect to sample preparation can be highly affected even for specimens prepared from a single sample assuming that a different dilution ratio (binder/material) is applied during sample preparation.

The absorption of X-rays pass through a sample is determined by:

$$\mu(E) = \sum_{i=1}^{i=nel} w_i \mu_i(E)$$

which is the mass attenuation coefficient of the specimen (typically expressed in $cm^2/g$) which is directly related to the composition of the specimen since it contains the weight fractions of all elements in the specimen $w_i$ and the mass absorption coefficient of each element $\mu_i$ (E) at the excitation/diffraction energy E.

Other relevant definitions used in this and other equations in this document are collected below for convenience:

| | |
|---|---|
| $w_{fl}$ | The weight fraction of the predetermined component |
| $I_d$ | The intensity (kcps) of scattered photons recorded by the detector |
| $M_{fl} = \dfrac{e^{-\mu \cdot \rho \cdot d \cdot cosec\psi_2} - e^{-\mu \cdot \rho \cdot d \cdot cosec\psi_1}}{\mu \cdot (cosec\psi_1 - cosec\psi_2)}$ | Matrix/thickness correction term |
| $\mu' = \mu \cdot cosec\,\psi_1$ | Effective mass absorption coefficient ($cm^2/g$) for the incident photons |
| $\mu'' = \mu \cdot cosec\,\psi_2$ | Effective mass absorption coefficient ($cm^2/g$) for the scattered photons |
| $\psi_1$ | The angle formed between the direction of the incident photons and the surface of the sample (incident angle). |
| $\psi_2$ | The angle formed between the |

-continued

| | |
|---|---|
| | direction of the diffracted photons and the surface of the sample (exit angle - diffraction channel). |
| $\psi_3$ | The angle formed between the direction of the scattered photons and the surface of the sample for a shifted detector angle (exit angle - background channel). |
| $G_{fl}$ | The geometry factor for the diffraction channel |
| $G_{bg}$ | The geometry factor for the background channel |
| $\theta_d$ | Diffraction angle |
| $\sigma$ | Scattering cross section |

Consider X-rays incident on a sample at an incident angle $\psi_1$ and further consider the X-rays diffracted by a particular component at an exit angle $\psi_2$ as illustrated in FIG. 1.

An example will be presented in this section for assistance in understanding the mathematics. In the example the particular (pre-determined) component is free lime though the method is equally applicable to other components. Assuming the incident radiation is the Ag-Ka line then the first order diffraction will be expected to be at a diffraction angle $2\theta_{fl}=13.3°$. Therefore, in this example and assuming an incident angle $\psi_1=57°$ the exit angle $\psi_2=57°+13.3°=70.3°$ for the diffraction peak.

At the exit angle corresponding to the diffraction peak, the intensity that will be observed by the scintillation detector will be given by:

$$I_d(\theta_{fl}) = G_{fl} \cdot \text{cosec}\psi_1 \cdot [w_{fl} \cdot \sigma_{fl}(\theta_{fl}) + (1-w_{fl}) \cdot \sigma_{oth}(\theta_{fl})] \cdot M_{fl} \quad (1)$$

Where:

$$M_{fl} = \frac{e^{-\mu \cdot \rho \cdot d \cdot \text{cosec}\psi_2} - e^{-\mu \cdot \rho \cdot d \cdot \text{cosec}\psi_1}}{\mu \cdot (\text{cosec}\psi_1 - \text{cosec}\psi_2)} \quad (1a)$$

is the self-absorption term at the angle $\theta_{fl}$.

Note that $\sigma$ is the scattering cross section of the predetermined component measured at a diffraction peak (free lime in this case) and $\sigma_{oth}$ the scattering cross section of all other components.

If the detector and collimator is now rotated by $\Delta\psi$ in the range 0.5° to 5°, for example 1° we will be observing the scattered intensity at an angle $2\theta_{bg}=2\theta_{fl}+1°$ which will be expressed as follows:

$$I_d(\theta_{bg}) = G_{bg} \cdot \text{cosec}\psi_1 \cdot [w_{fl} \cdot \sigma_{fl}(\theta_{bg}) + (1-w_{fl}) \cdot \sigma_{oth}(\theta_{bg})] \cdot M_{bgl} \quad (2)$$

where:

$$M_{fl} = \frac{e^{-\mu \cdot \rho \cdot d \cdot \text{cosec}\psi_3} - e^{-\mu \cdot \rho \cdot d \cdot \text{cosec}\psi_1}}{\mu \cdot (\text{cosec}\psi_1 - \text{cosec}\psi_2)} \quad (2a)$$

Notice, that the matrix absorption term is slightly modified since it contains now the exit angle $\psi_3=\psi_2+1°$.

For the evaluated experimental arrangement $\psi_1=57°$ and the exit angles $\psi_2=57°+13.3°=70.3°$ and $\psi_3=71.3°$.

Forming the ratio between the measured intensity in the two channels we obtain:

$$\frac{I_d(\theta_{fl})}{I_d(\theta_{bg})} = \frac{G_{fl}}{G_{bg}} \cdot \frac{[w_{fl} \cdot \sigma_{fl}(\theta_{fl}) + (1-w_{fl}) \cdot \sigma_{oth}(\theta_{fl})]}{[w_{fl} \cdot \sigma_{fl}(\theta_{bg}) + (1-w_{fl}) \cdot \sigma_{oth}(\theta_{bg})]} \cdot \frac{M_{fl}}{M_{bg}} \quad (3)$$

or equivalently:

$$\frac{I_d(\theta_{fl})}{I_d(\theta_{bg})} = \frac{G_{fl}}{G_{bg}} \cdot \frac{\sigma_{oth}(\theta_{fl})}{\sigma_{oth}(\theta_{bg})} \cdot \frac{\frac{w_{fl}}{1-w_{fl}} \frac{\sigma_{fl}(\theta_{fl})}{\sigma_{oth}(\theta_{fl})}+1}{\frac{w_{fl}}{1-w_{fl}} \frac{\sigma_{fl}(\theta_{bg})}{\sigma_{oth}(\theta_{bg})}+1} \cdot \frac{M_{fl}}{M_{bg}} \quad (3a)$$

However, assuming the first measured intensity is a diffraction peak then the intensity corresponding to this free lime peak at an exit angle $\psi_3$ i.e. $\theta_{bg}$ is small. In this case, therefore, the first term in equation (3b) below is small and we may write:

$$\frac{w_{fl}}{1-w_{fl}} \frac{\sigma_{fl}(\theta_{bg})}{\sigma_{oth}(\theta_{bg})}+1 \approx 1 \quad (3b)$$

This applies in particular for the example of free lime peak. For normal free lime ranges (0.1%-2.0%) the first term of the sum in the denominator should be significantly lower than $10^{-3}$. This originates from the value of the weight fraction term and the fact that the probability of scattering for the free lime crystals far from their corresponding diffraction angle for Ag-Ka is at least one order of magnitude lower.

Under these considerations the ratio now becomes:

$$\frac{I_d(\theta_{fl})}{I_d(\theta_{bg})} = G \cdot \frac{\sigma_{oth}(\theta_{fl})}{\sigma_{oth}(\theta_{bg})} \cdot \left[\frac{w_{fl}}{1-w_{fl}} \frac{\sigma_{fl}(\theta_{fl})}{\sigma_{oth}(\theta_{fl})}+1\right] \cdot \frac{M_{fl}}{M_{bg}} \quad (4)$$

where $G=G_{fl}/G_{bg}$ is the ratio of the geometry factors.

Figure 4:
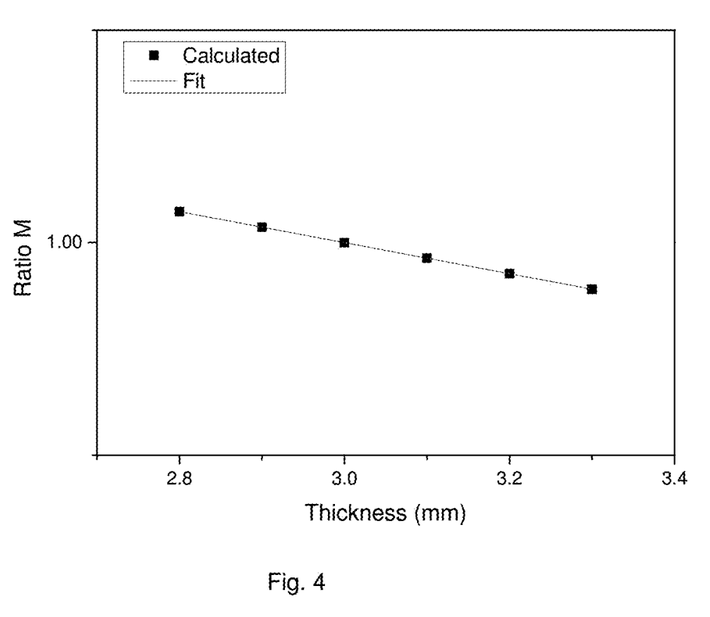
FIG. 4 shows the ratio of Matrix correction terms as a function of sample thickness d.

The formula is still far from a simple linear relation and includes the ratio of the self-absorption terms M. FIG. 4 illustrates the ratio of the self-absorption terms M in the example free lime case as function of thickness d for a typical clinker composition with $\mu \approx 5.0$ cm$^2$/g, $\rho \approx 2.0$ g/cm$^3$ and for thickness values d ranging from 2.8 mm to 3.2 mm.

As can be seen in FIG. 4, a change of 300 μm in the sample thickness will affect the ratio of the mass absorption coefficients by about 0.1%. In this sense, the intensity ratio becomes much more insensitive to sample thickness variations.

Thus, the inventors have shown that it is a reasonable approximation to rewrite equation (4) as:

$$\frac{I_d(\theta_{fl})}{I_d(\theta_{bg})} = G \cdot \frac{\sigma_{oth}(\theta_{fl})}{\sigma_{oth}(\theta_{bg})} \cdot \frac{w_{fl}}{1-w_{fl}} + G \cdot \frac{\sigma_{oth}(\theta_{fl})}{\sigma_{oth}(\theta_{bg})} \quad (5)$$

If the composition of the sample remains nearly constant then the ratios of equivalent cross sections $\sigma_{fl}(\theta_{fl})/\sigma_{oth}(\theta_{bg})$ and $\sigma_{oth}(\theta_{fl})/\sigma_{oth}(\theta_{bg})$ will also remain constant. In such case the intensity ratio can be written only as function of the free lime weight fraction:

$$\frac{I_d(\theta_{fl})}{I_d(\theta_{bg})} = A \cdot \frac{w_{fl}}{1 - w_{fl}} + B \quad (5a)$$

Generally speaking the ratio of two linear functions is not a linear but a rational one. With the variable change $$W = \frac{w_{fl}}{1 - w_{fl}} \quad (6)$$

we may rewrite:

$$\frac{I_d(\theta_{fl})}{I_d(\theta_{bg})} = A \cdot W + B \quad (7)$$

Thus, the ratio of intensities can be considered to be a linear function of the ratio W where $$W = \frac{w_{fl}}{1 - w_{fl}}$$

and $w_{fl}$ is the weight fraction of the component of interest.

In other words, by making two measurements as described, it is possible to avoid the effect of the term M which otherwise makes quantitative measurement very difficult indeed without significant efforts to calibrate.

Note that the method does not simply subtract off a background correction, i.e. the method does not measure the background intensity near a peak to determine the peak height by subtraction. Instead, the method uses an intensity ratio of the free lime peak and a suitable neighboring position since by using the intensity ratio the effect of the matrix correction term M is effectively compensated for.

Implementation

Figure 5:
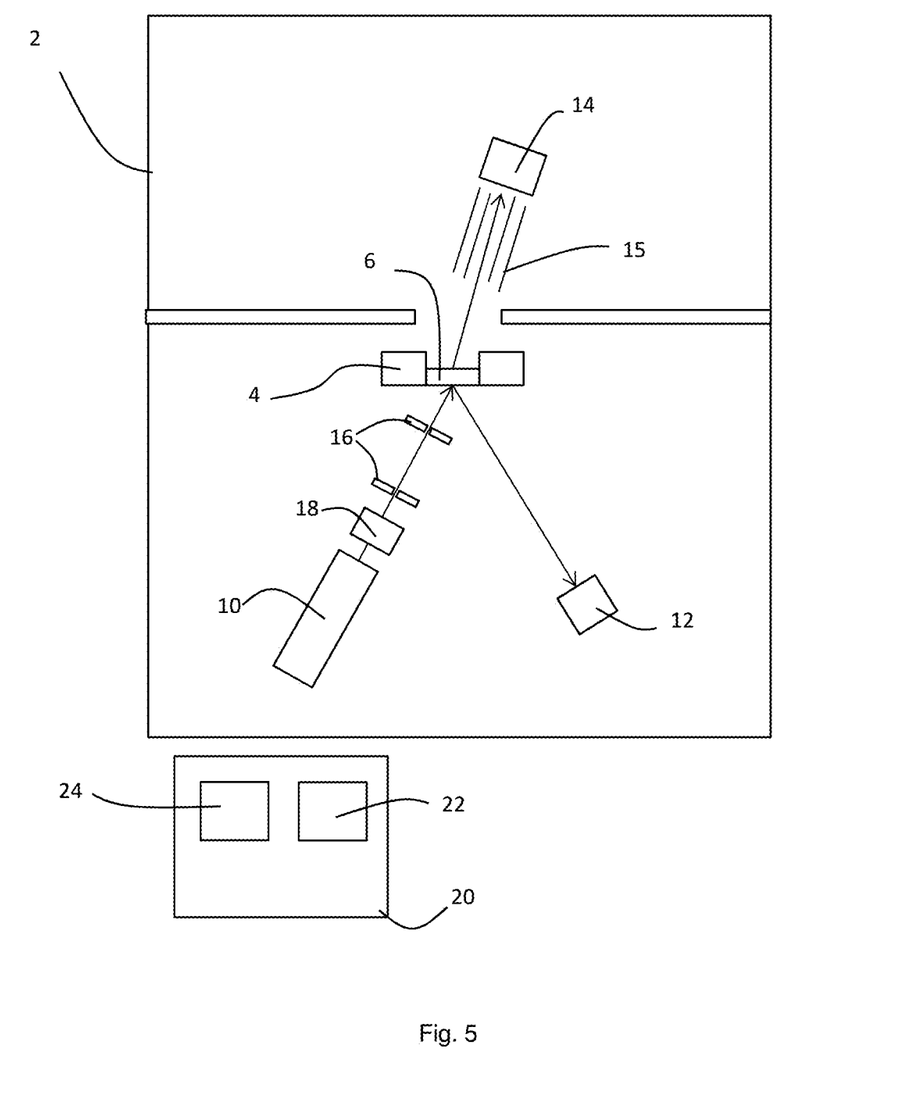
FIG. 5 shows apparatus used to take measurements in a first embodiment of the invention.

Equations (6) and (7) can be used to make measurements in the system illustrated in FIG. 5.

An X-ray apparatus 2 has a sample stage 4 for holding a sample 6.

An X-ray source 10 is mounted below the sample stage 4. Conveniently, although not required in this method, a fluorescence X-ray detector 12 for measuring X-ray fluorescence is provided below the sample stage 4. The fluorescence X-ray detector may be an energy dispersive detectors measuring X-ray intensity as a function of energy or a wavelength dispersive X-ray system consisting of goniometer, masks, crystals, collimators and detectors for selecting X-rays only of a particular wavelength. A transmission X-ray detector 14 is mounted above the sample stage 4 on a goniometer so that it can measure diffracted X-rays as a function of angle.

A number of other components are provided, including collimator 16 and filter 18. The collimator 16 is required for diffraction measurements only and may be removed for XRF measurements. Further, note collimator 15 for selecting only X-rays diffracted by the sample at a particular angle. Collimator 15 is mounted between the sample and the transmission X-ray detector and is likewise mounted on a goniometer for rotation to allow the selection of different angles. In practice, all that is required to measure the background intensity in the correction measurement (see below) is to rotate the collimator 15 if X-ray detector 14 has a sufficiently large X-ray input window.

The apparatus is under control of controller 20 which includes a memory 22 and processor 24.

In the embodiment shown, the X-ray source 10 is arranged to emit Ag-Kα radiation and the filter 18 is arranged to filter out the Ag-Kb line and possibly also to filter out continuum radiation. The filter may be a multilayered filter including layers of Rh or Pd to filter out the Ag-Kb line and other layers such as Ag to filter out the continuum. Other high atomic number (Z) layers may be used as well as the Ag or additional to the Ag.

In use, a sample 6 is prepared by the pressed powder method. A powder is compressed together with wax binder in a ring to form a sample which is mounted on the sample stage. In the specific example, the sample is a clinker sample and the predetermined component which is to be measured is free lime.

A measurement of the intensity at the diffraction peak $2\theta_{fl} = 13.3°$ is then measured in transmission with the source located to provide an incident angle $\psi_1$ and the transmission X-ray detector located to provide an exit angle $\psi_2 = \psi_1 + 13.3°$. Then, the transmission X-ray detector 14 and collimator 15 are rotated by $\Delta\psi$ to a new exit angle $\psi_3$ and a correction measurement of intensity made with the detector at an exit angle $\psi_3$ without moving the X-ray source 2.

The intensity ratio of the measured intensity divided by the correction intensity is then obtained and the controller determines the weight fraction of the component of interest, here free lime, from the linear relation between the ratio and W (equation 7) and then converting this to a free lime concentration using equation (6).

In order to obtain the calibration curve calibration is carried out with a number of samples of known concentration. Each of these samples is measured using the above method and the calibration curve of concentration against intensity ratio is obtained by a fit of intensity ratio to the parameter W.

These measurements and the calibration are all carried out controlled by code stored in memory 24 which controls processor 22 in controller 20 to control the apparatus 2 to carry out the measurements.

EXAMPLES

An experimental example was carried out to test the validity of the approximations made, as well as the applicability of the method.

Figure 6:
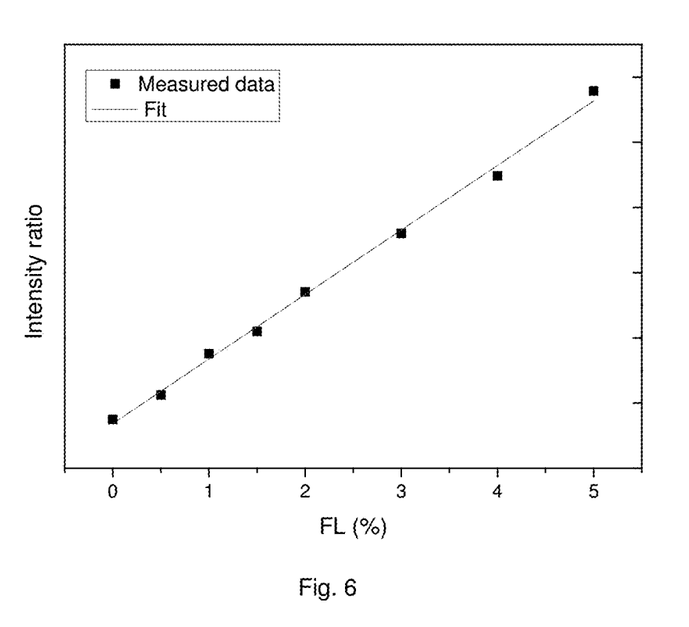
FIG. 6 shows a calibration curve of the percentage of free lime against intensity ratio.

A set of pressed pellets were prepared. The set consisted of specimens originating from a clinker matrix spiked with appropriate free lime (FL) quantities to yield final FL concentrations equal to 0%, 0.5% 1%, 1.5%, 2%, 3%, 4% and 5%. Measurements were taken as described above with a view to testing whether the expected linear relationship of measured intensity ratio held. The measurements were performed with the diffraction intensity measured at an $\psi_2 = 70.3°$ and near XRD (XRDBG) at an angle $\psi_3 = 71.3°$ with an incident angle The calibration curve for the FL component is shown in FIG. 6. Note that the calibration curve using the method discussed above is well defined and linear.

Further experiments of similar nature confirm the results above and show that the ratio between the measured intensity at the free lime channel and a small angular deviation from that channel is nearly constant for a range of thickness values, so the ratio method discussed here can be used.

An advantage of this method is that sample inhomogeneities are not particularly important since the X-ray beam incident and diffracted interacts with the same sample volume for both measurements. Further, the method cancels out most instrumental drift by the use of the intensity ratio which can avoid the need for further complex calibration.

Note that when measuring free lime in clinker samples, there is an interest in other components of those cement samples. XRF using fluorescence X-ray detector 12 may be carried out to determine the elemental composition of those samples without removing the samples from the apparatus. In particular, measurement of Ca, Fe, Al and Si with the assumption that these elements are present in the samples in their oxidised form allows for measurement of all components of clinker samples.

Those skilled in the art will appreciate that the methods and apparatus described above can be varied as required.

Although the measurements have been discussed above with reference to the measurement of the free lime diffraction peak in clinker samples, the method presented is not limited to that example and other examples where a matrix correction is required may also be measured in the same way.

The invention claimed is:

1. A method of X-ray analysis comprising:
    making an X-ray diffraction measurement in transmission by directing X-rays from an X-ray source at an energy E onto a sample at an incident angle $\psi_1$ to the surface of the sample and measuring a diffraction intensity $I_d(\theta_d)$ of the diffracted X-rays at the energy E with a X-ray detector at an exit angle $\psi_2$ to the surface of the sample, a difference $2\theta_d$ between the incident angle and the exit angle corresponding to an X-ray diffraction peak of a predetermined component; and
    making a correction measurement of X-rays by measuring a background intensity of X-rays $I_d(\theta_{bg})$ at the energy E, with the difference $2\theta_{bg}$ between the incident angle and the exit angle deviating by 0.2 to 5° from the difference $2\theta_d$ corresponding to the X-ray diffraction peak; and
    calculating the quantity of the predetermined component from the intensity ratio $I_d(\theta_d)/I_d(\theta_{bg})$ of the diffraction intensity and the background intensity.

2. The method according to claim 1, wherein the step of making a correction measurement of X-rays uses incident X-rays directed onto the sample at the same incident angle $\psi_1$ to the angle used in the step of making an X-ray diffraction measurement and measures the background intensity of X-rays at an exit angle $\psi_3$ to the surface of the sample, where $\psi_3=\psi_2\pm\Delta\psi$ and $\Delta\psi$ is in the range 0.2 to 5°.

3. The method according to claim 1, wherein calculating the quantity of the predetermined component comprises obtaining the quantity of the predetermined component from a calibration curve linking the intensity ratio to the quantity of the predetermined component.

4. The method according to claim 1 wherein the predetermined component is free lime.

5. A method comprising
    obtaining a calibration curve relating the intensity ratio to concentration of the predetermined component by carrying out a method according to claim 1 for a plurality of samples each having a known concentration of the predetermined component; and
    measuring the quantity of a predetermined component in an unknown sample by carrying out a method according to claim 1 for the unknown sample.

6. An X-ray apparatus, comprising:
    a sample stage for supporting a sample extending substantially horizontally;
    an X-ray source located to direct X-rays to the sample stage;
    an X-ray detector located on the other side of the sample stage for measuring X-ray intensity of diffracted X-rays in a transmission geometry; and
    a controller;
    wherein the controller is arranged to cause the X-ray apparatus to carry out a method according to claim 1 on a sample mounted on the sample stage.

7. The method according to claim 2, wherein calculating the quantity of the predetermined component comprises using a linear relation between the intensity ratio and a calculated $$W = \frac{w_{fl}}{1 - w_{fl}}$$

where $w_{fl}$ is the weight fraction of the component of interest.

8. The method according to claim 5 further comprising fitting a straight line to the intensity ratio as a function of the concentration of the plurality of samples having a known concentration of the predetermined component.

9. The X-ray apparatus according to claim 6, further comprising a further X-ray detector located on the same side of the sample stage as the X-ray source for making X-ray fluorescence measurements of the sample.

* * * * *